United States Patent [19]
Kohrs et al.

[11] Patent Number: 5,658,337
[45] Date of Patent: Aug. 19, 1997

[54] INTERVERTEBRAL FUSION IMPLANT

[75] Inventors: Douglas W. Kohrs, Edina, Minn.;
Hansen A. Yuan, Fayetteville, N.Y.;
David W. Stassen, Edina, Minn.

[73] Assignee: Spine-Tech, Inc., Minneapolis, Minn.

[21] Appl. No.: 633,297

[22] Filed: Apr. 17, 1996

Related U.S. Application Data

[63] Continuation of Ser. No. 247,857, May 23, 1994, abandoned.

[51] Int. Cl.$^6$ .................................................. A61F 2/44
[52] U.S. Cl. .................................................. 623/17; 606/61
[58] Field of Search .............................. 623/17; 606/60, 606/61

[56] References Cited

U.S. PATENT DOCUMENTS

| | | | |
|---|---|---|---|
| 2,677,369 | 5/1954 | Knowles | 623/17 |
| 4,349,921 | 9/1982 | Kuntz . | |
| 4,501,269 | 2/1985 | Bagby . | |
| 4,743,256 | 5/1988 | Brantigan . | |
| 4,834,757 | 5/1989 | Brantigan . | |
| 4,878,915 | 11/1989 | Brantigan . | |
| 4,936,848 | 6/1990 | Bagby et al. . | |
| 4,961,740 | 10/1990 | Ray et al. . | |
| 5,015,247 | 5/1991 | Michelson . | |
| 5,026,373 | 6/1991 | Ray et al. . | |
| 5,055,104 | 10/1991 | Ray . | |
| 5,062,850 | 11/1991 | MacMillan et al. . | |
| 5,192,327 | 3/1993 | Brantigan . | |
| 5,294,391 | 3/1994 | McMillin . | |

OTHER PUBLICATIONS

International Search Report for Application No. PCT/US95/01655.

*Primary Examiner*—Robert A. H. Clarke
*Attorney, Agent, or Firm*—Merchant, Gould, Smith, Edell, Welter & Schmidt

[57] ABSTRACT

A intervertebral fusion implant includes first and second bearing surfaces which oppose cortical bone upon insertion of the implant into a bore formed between two vertebrae. The implant includes first and second ridges which extend from the bearing surface. The ridges extend through the cortical bone into cancellous bone. The ridges are provided with openings formed through the ridges. The openings are in communication with the interior of the implant.

13 Claims, 9 Drawing Sheets

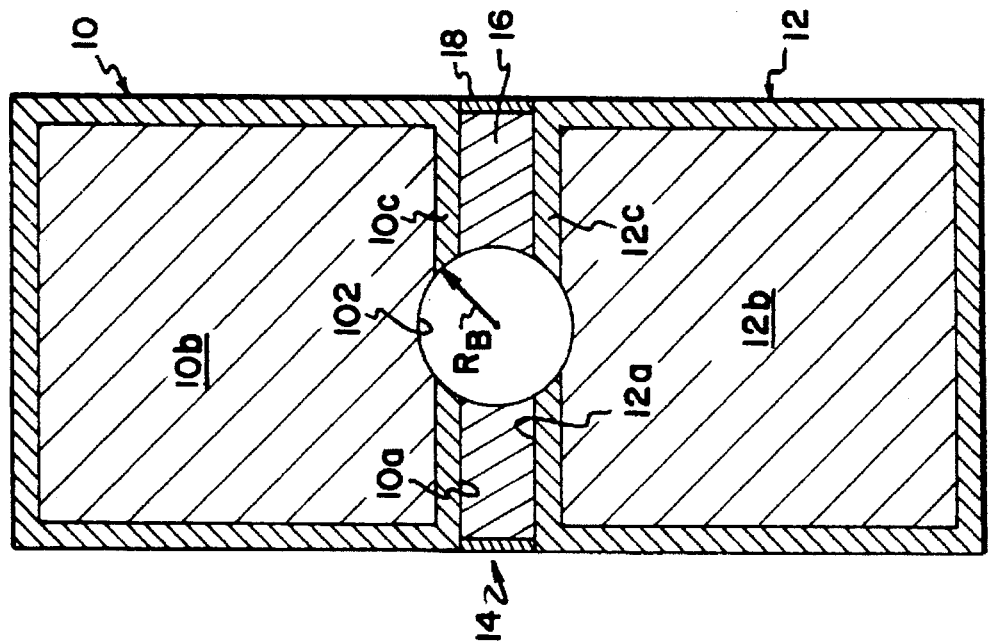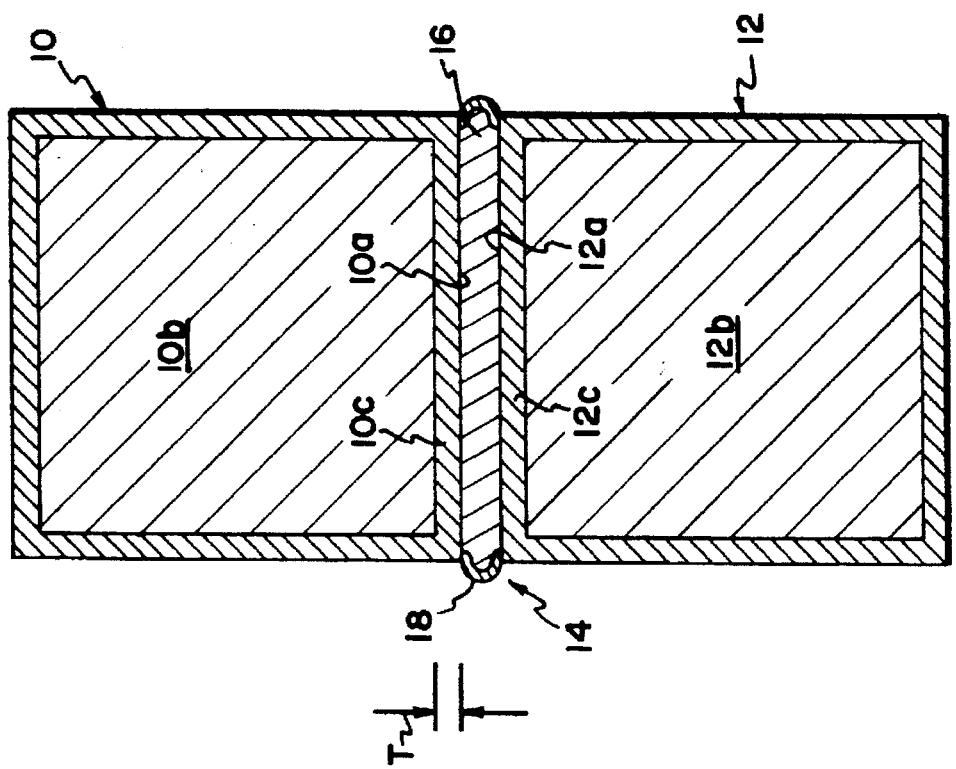

INTERVERTEBRAL FUSION IMPLANT

This is a CONTINUATION of application Ser. No. 08/247,857, filed May 23, 1994 now abandoned.

BACKGROUND OF THE INVENTION

1. Field of the Invention

This invention pertains to intervertebral fusion. More particularly, this invention pertains to an implant to facilitate fusion between two vertebrae.

2. Description of the Prior Art

Back pain is extremely debilitating. Individuals suffering from severe back pain are frequently precluded from the full enjoyment of life including gainful employment and leisure activities. In addition to the substantial human costs associated with back pain, society bears a substantial financial cost. Lost employment time adversely impacts on productivity as does medical insurance costs.

Frequently, the cause of back pain is traceable to diseased disc material between opposing vertebrae. When the disc material is diseased, the opposing vertebrae are not adequately supported.

In order to address back pain resulting from disc disease, prior art surgical techniques have been developed to fuse the opposing vertebrae. Such techniques include removing the diseased disc and packing the disc space with bone. The intent of such a procedure is for the packed bone to grow together and fuse with the bone of the opposing vertebra. If successful, the two opposing vertebrae are now rigidly linked thereby avoiding intervertebral instability.

In fusing opposing vertebrae, the prior art has developed surgical techniques and apparatus to facilitate interbody fusion as well as to permit stabilization of the vertebra while the fusion process is occurring. To this end, surgical implants have been developed.

An example of a surgical implant for facilitating interbody fusion is shown in U.S. Pat. No. 5,015,247 to Michelson dated May 14, 1991. Michelson uses a circular cross-section cylindrical implant which is of uniform diameter throughout its length and which includes an external thread. The implant is hollow and has holes formed through the cylindrical wall of the implant. The implant is placed within a prepared site between the vertebrae. The prepared site is a bore formed through the disc material as well as partially formed through the end plates of the opposing vertebrae. The implant is threaded into the bore and packed with bone chips or the like.

Another example of an interbody fusion device is shown U.S. Pat. No. 4,834,757 to Brantigan dated May 30, 1989. The Brantigan device is a parallelepiped plug which is forced into a complementarily shaped cavity formed between opposing vertebrae.

Prior art interbody fusion devices are not trouble free. For example, prior art devices suffer from uncontrolled subsidence of the device into the vertebral body. By subsidence, it is meant that after the implant is placed between the opposing vertebra, the implant migrates into the vertebral body. Also, in many prior art implants, direct bone apposition only occurs on two surfaces. In addition, unwanted invasion of disc or cartilage material into the implant may occur upon insertion. Such prior art devices typically have minimal surface area contact with the end plates of the vertebra. In addition to the above, such prior art devices have a geometry which prevents close placement when two implants are placed in a side-by-side relation within a common disc space. A prior art device to increase the density of implant placement is shown in U.S. Pat. No. 5,055,104 to Ray dated Oct. 8, 1991. In that patent, the device is a helical thread. Two such devices are placed side-by-side with the threads intermeshing.

It is an object of the present invention to provide an implant for use in interbody fusion. It is a further object of the present invention to provide such an implant which has reduced subsidence.

SUMMARY OF THE INVENTION

According to a preferred embodiment of the present invention, an implant is provided for facilitating intervertebral fusion between opposing vertebrae. The implant includes first and second bearing surfaces, each extending along a plane generally parallel to the longitudinal axis of the implant. The first and second bearing surfaces are spaced apart in generally parallel alignment. A first and second ridge extend from the first and second bearing surfaces, respectively. Openings are provided through both the first and second ridges with the openings in communication with an interior of the implant. The bearing surfaces and ridges are sized for the first and second bearing surfaces to oppose and abut cortical bone while the ridges extend into cancellous bone.

BRIEF DESCRIPTION OF THE DRAWINGS

FIG. 1 is a schematic view showing two vertebral bodies separated by a disc material;

FIG. 10 is an end view of two vertebrae formed with a bore there between and stretched apart to receive the implant of FIG. 2;

DESCRIPTION OF THE PREFERRED EMBODIMENT

Figure 1A:
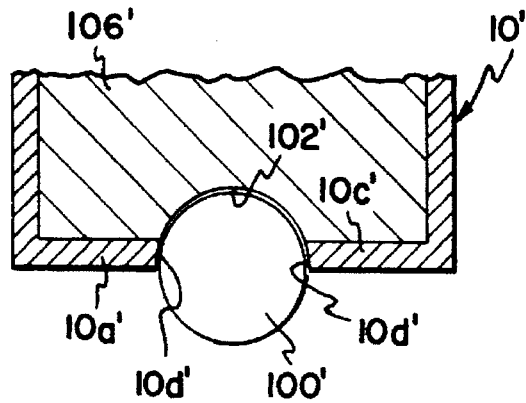
FIG. 1A is an end view of a prior art interbody device opposing a vertebra.

Referring now to the several drawing figures in which identical elements are numbered identically throughout, a description of the preferred embodiment of the present invention will now be provided.

With initial reference to FIG. 1, the implant of the present invention is intended for use in facilitating fusion between two vertebrae. FIG. 1 shows, in schematic format, an upper vertebra 10 and a lower vertebra 12. Each of the vertebrae 10,12 are vertically aligned and present opposing end plates 10a,12a. The end plates 10a,12a are separated by a disc 14. The disc 14 includes a fibrous inner material 16. The periphery of the disc 14 is a fibrous material conventionally referred to as the annulus 18. The interior of each of the vertebrae 10,12 consists of soft, cancellous bone 10b,12b. At the end plates 10a,12a, the vertebrae 10,12 include hard cortical bone layers 10c,12c. The cortical bone layers commonly have a thickness T of about 2 mm.

In interbody fusion placement, it is desirable to provide a bore to receive the fusion implant with the bore formed through the disc space 14 between the opposing vertebrae 10,12 and with the bore cutting through the cortical bone 10c,12c of the end plates 10a,12a. As a result, the cancellous bone 10b,12b of each of the vertebrae 10,12 is exposed and opposing the implant. Exposure of the cancellous bone is desirable since such cancellous bone 10b,12b is substantially laden with blood vessels. The cancellous bone is the most rapidly growing and forms the bone growth linking the vertebrae 10,12 upon completion of the spinal fusion therapy.

While exposure of the cancellous bone is desirable for the purpose of facilitating bone growth, the opposition of the implant to the cancellous bone increases the probability of subsidence since the cancellous bone is relatively soft and undesirable for the purposes of weight bearing.

Figure 1B:
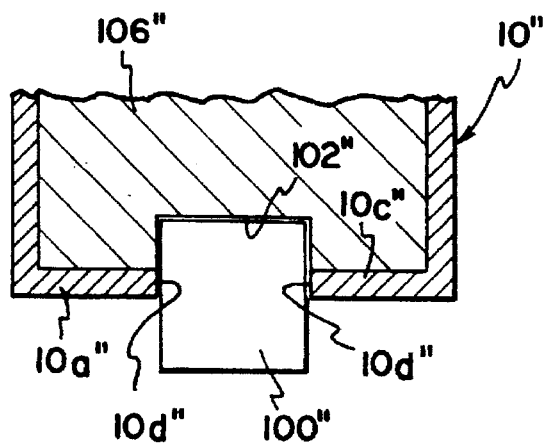
FIG. 1B is an end view of a different prior art intervertebral fusion device opposing a vertebra.
Figure 1C:
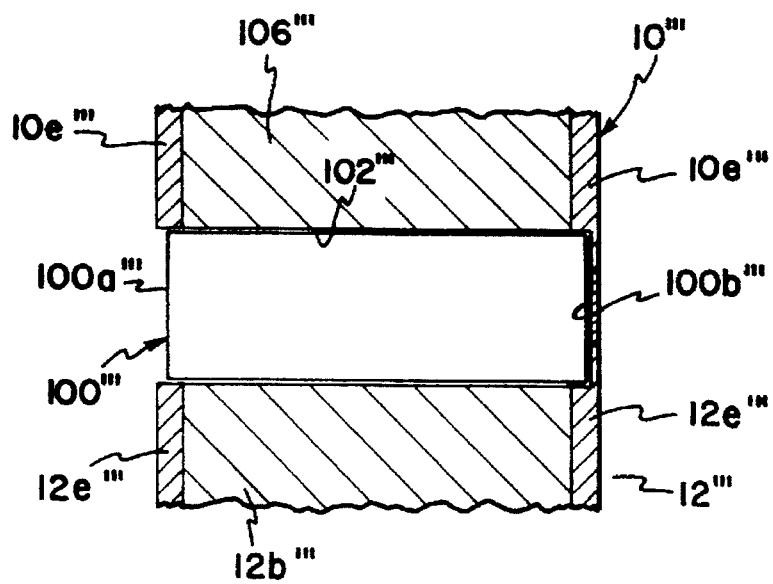
FIG. 1C is a side sectional view of an interbody device received between two vertebrae.
Figure 2:
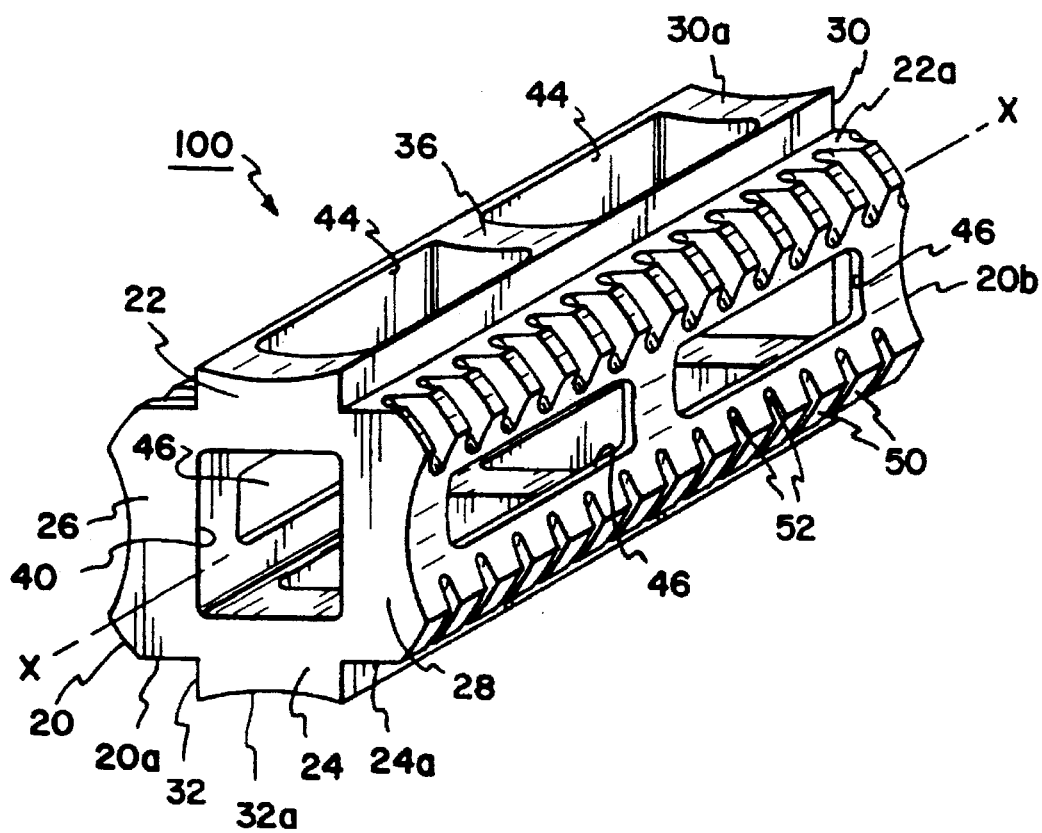
FIG. 2 is a front, right side and top perspective view of an implant according to the present invention.

With the anatomy thus described, disadvantages and problems associated with prior art implants can best be understood with references to FIGS. 1A, 1B and 1C. FIG. 1A shows an implant 100' positioned within a bore 102' formed in an upper vertebrae 10'. For purposes of illustration, a lower vertebrae is not shown in FIG. 1A but it will be appreciated that the lower vertebrae is similarly bored as upper vertebrae 10'. The intervertebral implant 100 shown in FIG. 1A is a generally cylindrical threaded implant such as that shown in U.S. Pat. No. 5,015,247. The bore 102' is an arc of a cylinder size to receive the implant 10'. So formed, the cortical bone 10c' of end plate 10a' is provided with angled surfaces 10d' opposing the implant 100'. The surfaces 10d' are the areas of greatest support since this is where the implant 10' bears against the cortical bone 10c'. Unfortunately, the surfaces 10d are of small surface area when compared to the total surface of the implant 100. Due to the angled surfaces 10d', the implant 100' is susceptible to slippage relative to the end plate 10a'. Upon occurrence of such slippage, subsidence of the implant 100' into the soft cancellous bone 10b' occurs. This subsidence causes the disc space to collapse and revert back to its pre-surgical condition.

FIG. 1B also shows a cross sectional view with an implant 100" such as that shown in U.S. Pat. No. 4,834,757. The implant 100" is substantially rectangular in cross section. The vertebra 10" is provided with a complementarily shaped bore 102". As a result, the cortical bone 10c" of the end plate 10a' opposes the implant 100", at generally vertical surfaces 10d". In this example, the cortical bone 10c" provides no bearing surface opposing migration of the implant 100" into the cancellous bone 10b'.

To prevent migration of either cylindrical or rectangular cross section implants into cancellous bone, certain prior art devices size the implant to rest on the vertical cortical bone surfaces of the vertebra. For example, FIG. 1C shows an implant 100''' (which could be either circular or rectangular in cross section), positioned between an upper vertebra 10''' and a lower vertebra 12'''. Each of the vertebrae 10''',12''' have outer vertical walls of cortical bone 10e''',12e'''. A bore 102''' is formed between the opposing vertebra 10''',12'''. The bore has a longitudinal length such that the ends 100a''' and 100b''' of implant 100''' bear directly against and oppose the cortical bone 12e''',10e'''. In this method of implantation, the implant 102' completely spans the soft cancellous bone 10b''',12b'''. In viewing FIG. 1C, the reader will note that in the absence of an implant length spanning the vertebra, the implant will subside into soft cancellous bone.

Examples of prior art teachings showing implants being sized and positioned to span soft cancellous bone and bear directly against cortical bone is shown in both U.S. Pat. No. 4,834,757 and U.S. Pat. No. 4,743,256. A disadvantage with the technique of having an implant sized and positioned such that it spans the soft cancellous bone and bears directly upon the outer cortical walls of the vertebra is that the bore forming operation for placement on the implant must be precisely controlled as to the length of the bore. The cortical layer against which the implant bears is very thin (approximately 2 millimeters). If the bore length is too small, the implant will not bear on the cortical bone. If the bore length is too great, the boring tool will pierce through the end of the vertebra. If the former occurs, subsidence is highly probable. The latter can be extremely dangerous. A boring tool piercing through a vertebra can puncture or sever important anatomical features such as the spinal cord, aorta or the like. If such anatomical features are damaged, severe consequences (including paralysis or death) can follow.

Having thus described the prior art implants and disadvantages associated with such implants, a description of an implant according to the present invention will now be described. It will be noted that the implant of the present invention provides full bearing on cortical bone while avoiding the need for a precisely controlled depth of cut.

With initial reference to FIGS. 2–9, an implant 100 according to the present invention is shown. The implant 100 includes a body 20 which is substantially square in cross section. The body extends along a longitudinal axis X—X.

The body 20 includes two generally flat upper and lower bearing walls 22,24. Bearing walls 22,24 are joined by side walls 26,28. Each of the bearing walls 22,24 present outwardly facing bearing surfaces 22a,24a. Each of the bearing surfaces 22a,24a extend generally parallel to each other and parallel to the longitudinal axis X—X.

Projecting perpendicularly away from the center of each of bearing walls 22,24 are raised ridges 30,32. Each of the ridges 30,32 extend parallel to axis X—X and project outwardly from the body 20. The ridges 30,32 are centrally positioned on the bearing surfaces 22a,24a such that the bearing walls 22,24 are exposed along opposite sides of each of the raised ridges 30,32. The ridges 30,32 terminate at concave faces 30a,32a.

The body 20 extends from a leading end 20a to a trailing end 20b. Intermediate ends 20a,20b, side walls 26,28 are joined by reinforcing ribs 36 (see FIGS. 4 and 5).

A bore 40 extends axially through body 20 and extends completely through the leading end 20a and trailing end 20b.

Figure 3:
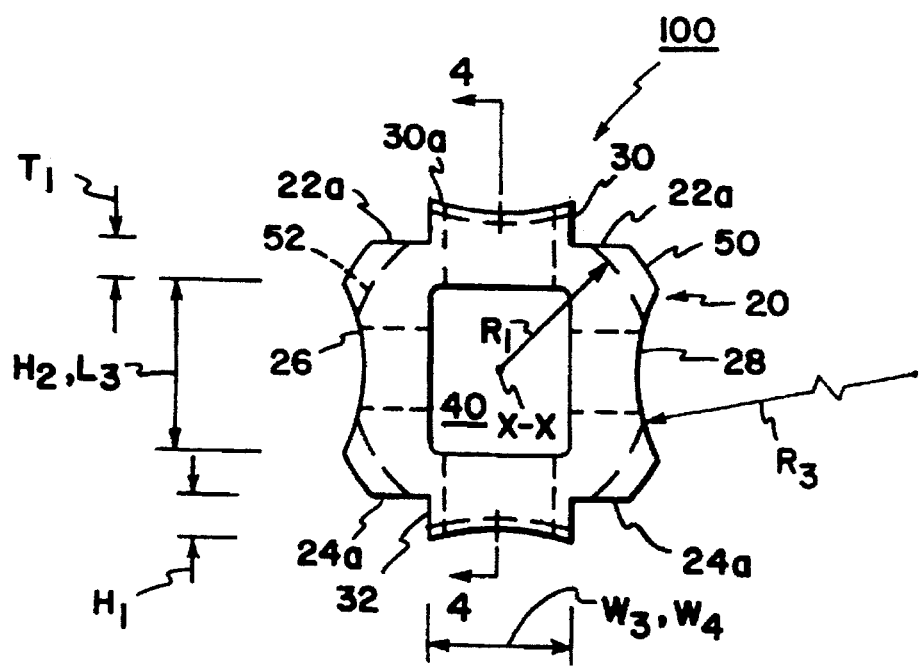
FIG. 3 is an elevation view of a trailing end of the implant of FIG. 2.
Figure 4:
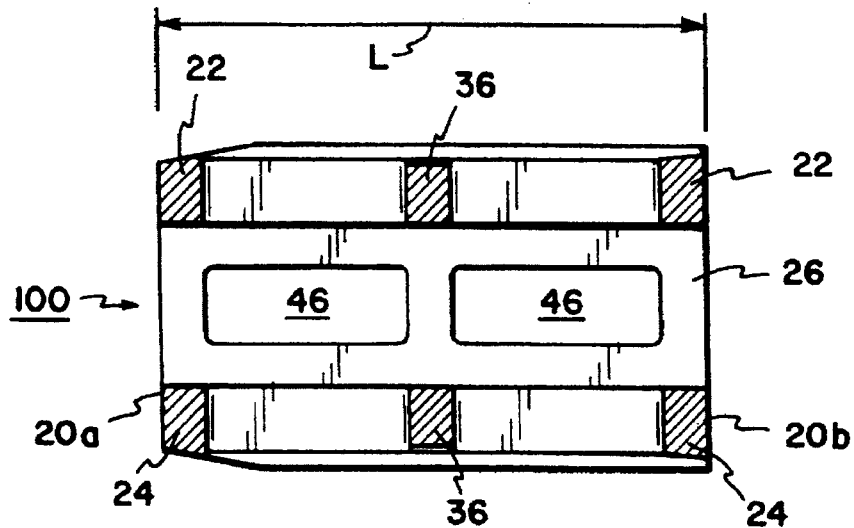
FIG. 4 is a view taken along line 4—4 of FIG. 3.
Figure 5:
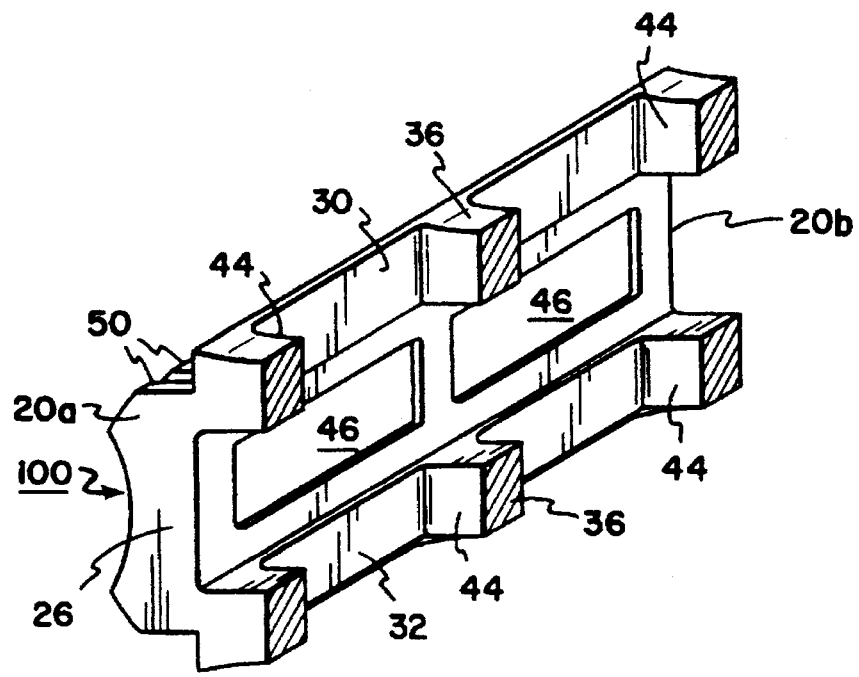
FIG. 5 is a perspective view of the sectioned implant of FIG. 4.
Figure 6:
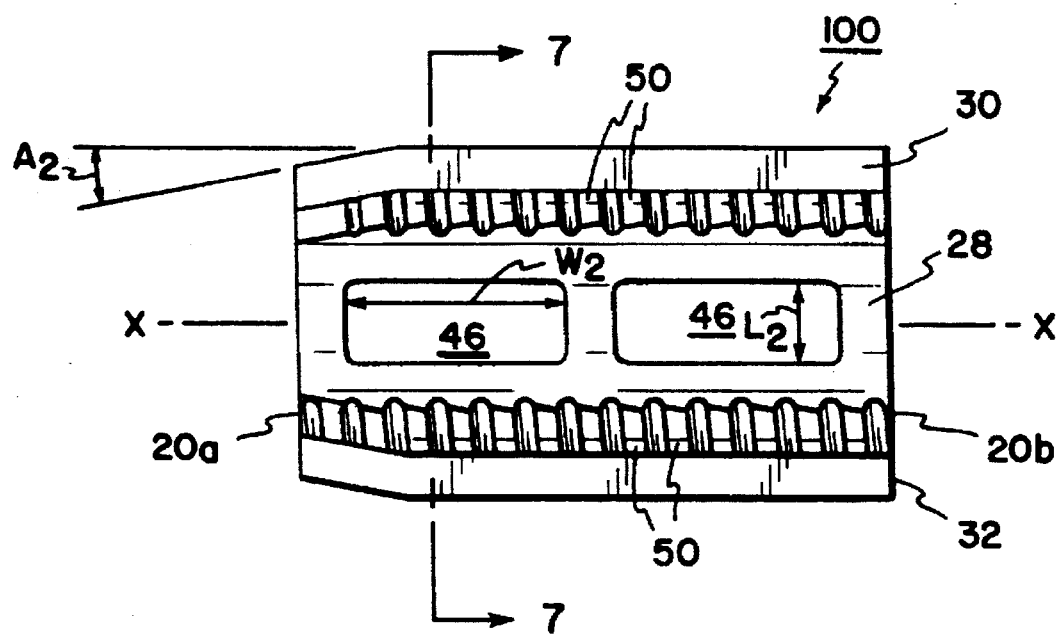
FIG. 6 is a side elevation view of the implant of FIG. 2.
Figure 7:
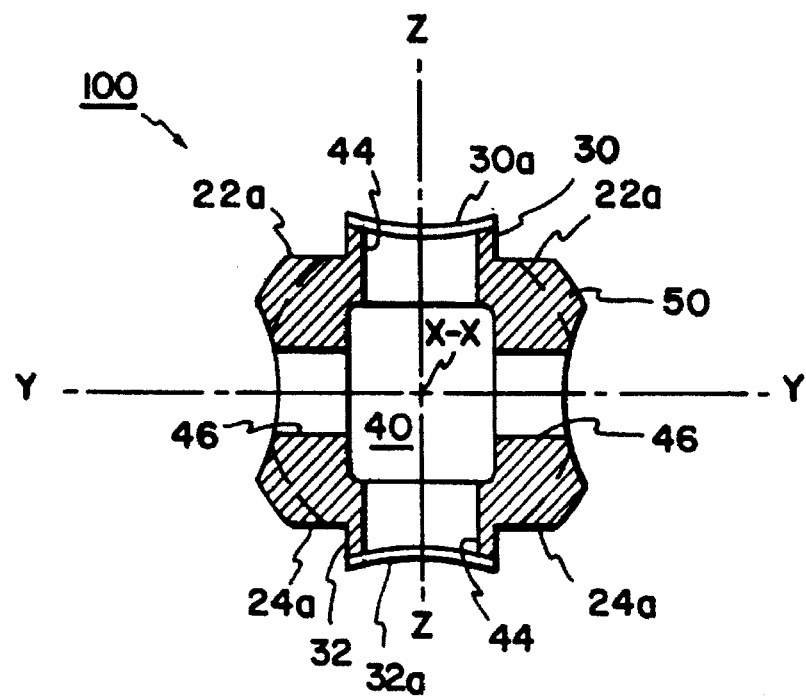
FIG. 7 is a view taken along line 7—7 of FIG. 6.
Figure 8:
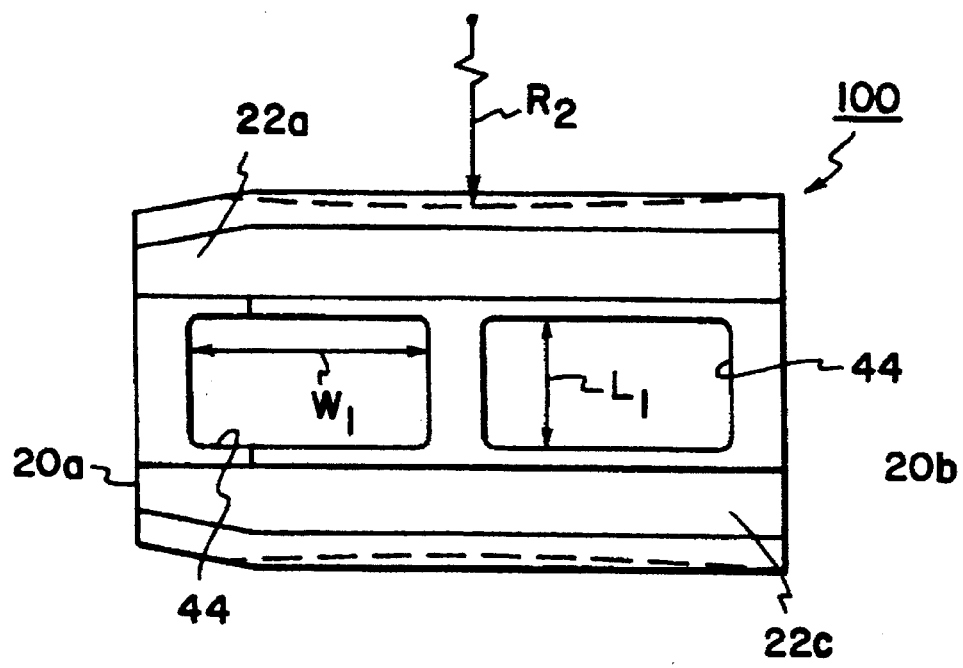
FIG. 8 is a top plan view of the implant of FIG. 2.

Bore 40 is generally rectangular in cross section as best shown in FIGS. 3 and 7.

Formed completely through ridges 30,32 and bearing walls 22,24 are a plurality of openings 44. Openings 44 have an axis Z—Z which is perpendicular to longitudinal axis X—X. Each of the openings 44 is in direct communication with bore 40.

Side walls 26,28 are concave and are provided with openings 46 therethrough in communication with chamber 40. Openings 46 extend along an axis Y—Y which is mutually perpendicular to axes Z—Z and X—X (see FIGS. 6 and 7).

At the edges of intersection between walls 22,24, 26 and 28, a plurality of anchor segments 50 are provided. Between each of the segments 50, a valley, or recess 52 is formed to define the anchor segments 50. The anchor segments 50 are portions of a helix pattern surrounding the axis X—X. Also, as best shown in FIG. 3, the valleys 52 reside on the arc of a circle having radius $R_1$ from axis X—X.

Figure 9:
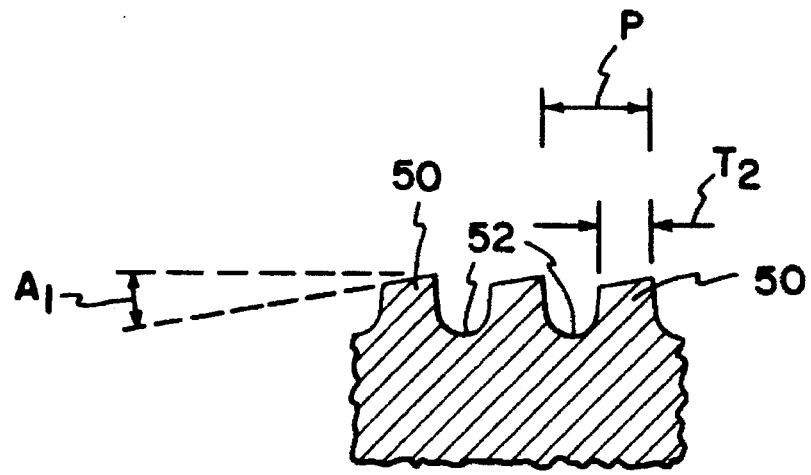
FIG. 9 is an enlarged view of a portion of the anchor detail of FIG. 6.

As shown best in FIG. 9, each of the anchor segments 50 is generally square in cross section with an end of the anchor 50 having an angled surface set at an angle $A_1$ relative to a line parallel to the axis X—X and slanted downwardly towards the leading end 20a. In a preferred embodiment, angle $A_1$ is 10°.

In a preferred embodiment, the cross sectional area of the implant is not uniform throughout its longitudinal dimension. With best reference to FIGS. 3 and 8, the outer faces 30a,32a of the ridges 30,32 and the side walls 26,28 are radiused inwardly as indicated at radii $R_2,R_3$. The benefits of the radii $R_2,R_3$ will be more fully described. $R_3$ equals the outside diameter of anchors 50. Further, the leading end 20a is provided with a taper angle $A_2$ (FIG. 6) which, in a preferred embodiment, is 10°.

As will be more fully described, the implant 100 is placed within a bore formed between two vertebra. The formation of the bore relative to the sizing of the implant is important for reasons that will become apparent. Accordingly, for the purposes of illustrating a preferred embodiment, the presently anticipated dimensions of the implants 100 will be given. It will be appreciated that various sizes of implant 100 will be available to accommodate different sized patients and different regions in the spine.

1. Length of implant L (FIG. 4): 28 millimeters;
2. Size of bores 44 ($L_1 \times W_1$, see FIG. 8): 0.416 inches by 0.216 inches;
3. Size of bores 46 ($L_2 \times W_2$, see FIG. 6): 0.416 inches by 0.150 inches;
4. Radius $R_1$ (FIG. 3) from axis X—X to valleys 52: 7.5 millimeters;
5. Size of cross section of bore 40 ($W_3 \times L_3$): 7 millimeters by 8 millimeters;
6. Width ($W_4$, see FIG. 3) of ridges 30,32: 7 millimeters;
7. Height ($H_1$, see FIG. 3) of ridges 30,32: 1 millimeter;
8. Height ($H_2$, FIG. 3) of convex area of side walls 26,28: 8 millimeters;
9. Thickness ($T_1$, FIG. 3) of bearing walls 26,28: 2 millimeters;
10. Pitch (P, FIG. 9) of anchors 50: 2.3 mm;
11. Thickness ($T_2$, FIG. 9) of anchors 50: 1 mm.
12. Radius $R_2$ (FIG. 8): 190 mm; and
13. Radius $R_3$ (FIG. 3): 8.75 mm.

To place the implant 100 between the vertebra 10,12 attention is now directed to FIG. 10. The vertebra 10,12 are distracted to stretch the annulus 18. A bore 102 is formed with its cylindrical axis extending parallel to and centrally positioned between the end plates 10a,12a. The bore 102 is sized for its radius $R_B$ to be equal to the radius ($R_1$) of the implant 100 (as shown in FIG. 3) to the valleys 52. The implant 100 and bore 102 are sized such that the radius $R_B$ will extend through the cortical layers 10c,12c without extensive penetration into the soft cancellous bone 10b,12b.

For the reasons that will become apparent, bore 102 must be precisely sized and accurately positioned with the axis of the bore 102 centrally positioned between the end plates 10a,12a and parallel to the end plates 10a, 12a. A surgical method and kit for accomplishing such an accurate formation of a bore between vertebra is the subject of commonly assigned and co-pending U.S. patent application Ser. No. 08/015,863, filed Feb. 10, 1993.

Figure 13:
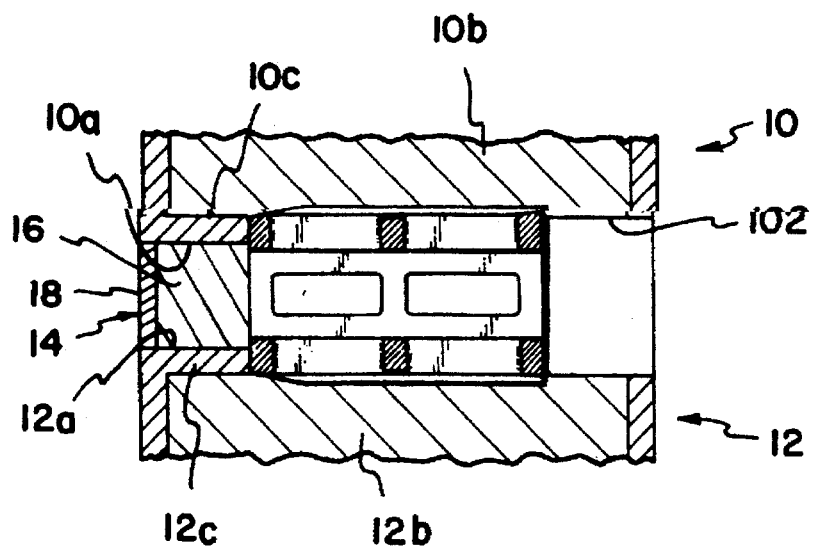
FIG. 13 is a side sectional view of an implant shown inserted between two vertebrae.

With bore 102 thus formed, the implant 100 is inserted into the bore 102 with the leading end 20a first introduced into the bore 102. The implant 100 is rotated about its axis X—X to advance the implant 100 into the bore 102 to the position shown in FIG. 13. Alternatively, implant 100 need not be rotated but simply can be impacted by driving it axially along its axis X—X. The implant 100 is positioned such that upon full insertion into the bore 102, openings 44 are directed toward the soft cancellous bone 10b,12b. The openings 46 are directed toward the space formerly occupied by removed disc material 16.

Figure 11:
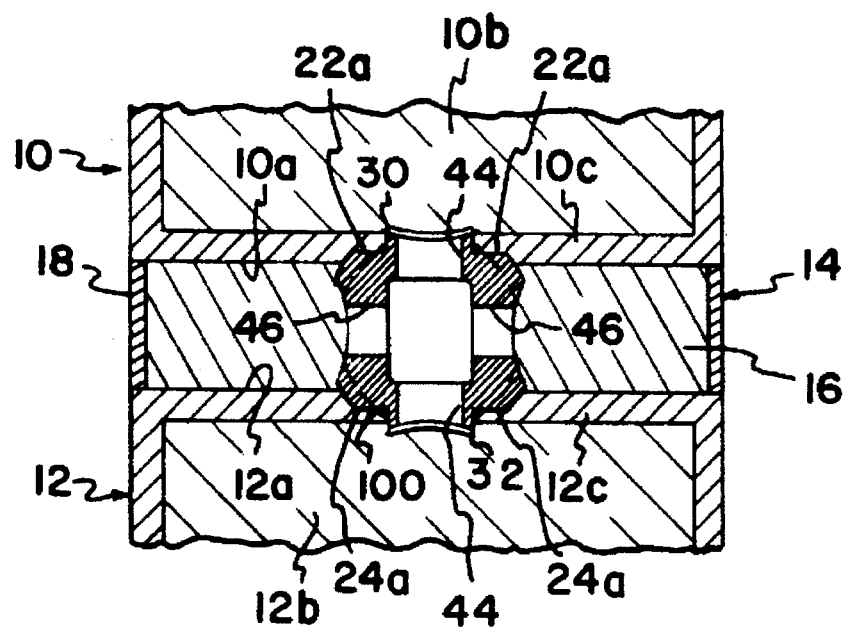
FIG. 11 is the view of FIG. 10 showing the implant of FIG. 2 inserted within the bore of FIG. 10.

With the radius $R_B$ of the bore selected to equal the radius $R_1$ to the valleys 52, after insertion of the implant, the bearing surfaces 22a,24a directly oppose and abut the cortical layer 10c,12c of the end plates 10a,12a (see FIG. 11). Also, with the relative sizing of the bore 102 thus described, the ridges 30,32 protrude beyond the cortical bone layer 10c,12c into the soft cancellous bone 10b,12b. With this structure and positioning of the implant 100, a surgeon can place bone chips within the bore 40. Accordingly, the bone 10b,12b is fused together by a bone column formed through the aligned bores 44,40. The load bearing of the surfaces 22a,24a against the cortical bone 10c,12c prevents subsidence of the implant 100 into the cancellous bone 10b,12b. The bearing surfaces 22a,24a are parallel to the implant 100 as opposed to current devices where a rounded surface contacts the implant 100 at an angle (e.g., U.S. Pat. No. 5,015,247) or rectangular devices where there is no end plate contact except at the extreme ends of the implant (e.g., U.S. Pat. No. 4,834,757). Also, the present implant 100 has non-threaded ridges 30,32 that project through the end plate 10a 12a and directly contact the cancellous bone 10b,12b. The surface area of the bores 44 is made as large as possible while permitting structural integrity to the implant 100 to provide maximum porosity to cancellous bone growing through the implant 100.

Figure 12:
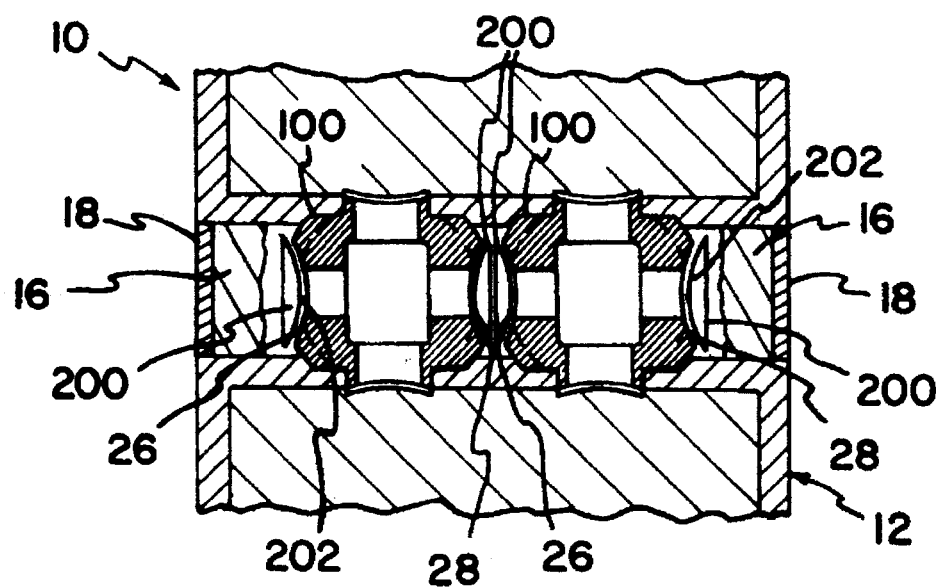
FIG. 12 is a view similar to that of FIG. 11 showing two implants disposed between opposing vertebrae.

In FIG. 11, a single implant 100 is shown inserted. In many applications (particularly in the lumbar region of the spine), two implants disposed in parallel alignment are preferred. Such a positioning is shown in FIG. 12. Also, in FIG. 12, it will be noted that the implants 100 are in close proximity. The closeness of proximity is attained by the concave side walls 26,28.

Normally, with convex side walls such as that shown in U.S. Pat. No. 5,015,247, implants cannot be placed with their axes in close proximity. Also, with threaded convex side walls, the implants of U.S. Pat. No. 5,015,247 cannot be allowed to touch. If the second implant to be inserted touches the first previously inserted implant, the second implant can cause the first implant to unscrew as the second implant is advanced. This creates a potentially dangerous situation where the previously inserted implant can be inadvertently unthreaded into a major vessel or the spinal cord. As a result in certain regions of the spine, only one implant can be placed while two would otherwise be desirable.

With the concave side walls 26,28, the present implants can be placed in closer proximity increasing the likelihood that two implants can be used at any disc level.

In the embodiment of FIG. 12, bone dowels 200 are positioned between both implants 100 and opposing the side walls 26,28 of the implants 100 on both sides thereof. The dowels have convex acurate outer surfaces 202 shaped to conform with the concave surfaces of the side walls 26,28. Bone dowels 200 are placed on the exterior side walls such that all bores 46 are in direct opposition to a bone dowel 200. With this application, disc material 16 is blocked by the bone dowels 200 from entering into the interior of the implants 100 and interfering with bone growth through the implants 100. Further, the bone growth through the bores 44,40 fuses with the bone growth through the side bores 46 and fuses with the bone dowels 200. Accordingly, the linkage between the vertebra 10,12 is enhanced since each of the implants 100 is cross linked.

Figure 14:
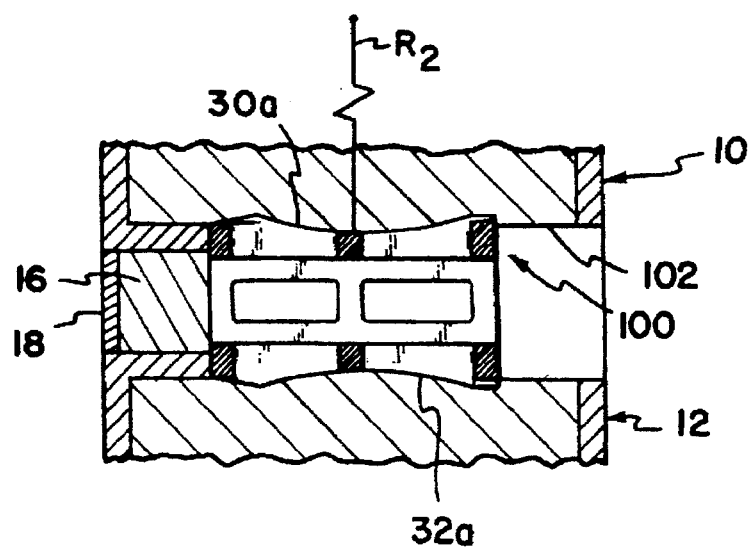
FIG. 14 is a schematic representation of the view of FIG. 13 showing radiused surfaces of the implant in great exaggeration for purpose of illustration.

FIG. 14 illustrates the value of the non-uniform cross-section of implant 100. Namely, the dip $R_2$ (shown exaggerated in FIG. 14 for purpose of illustration) in both of the walls 30a,32a and the side walls 26,28 prevents movement of the implant 100 along its axis X—X after the bone growth is achieved.

Figure 15:
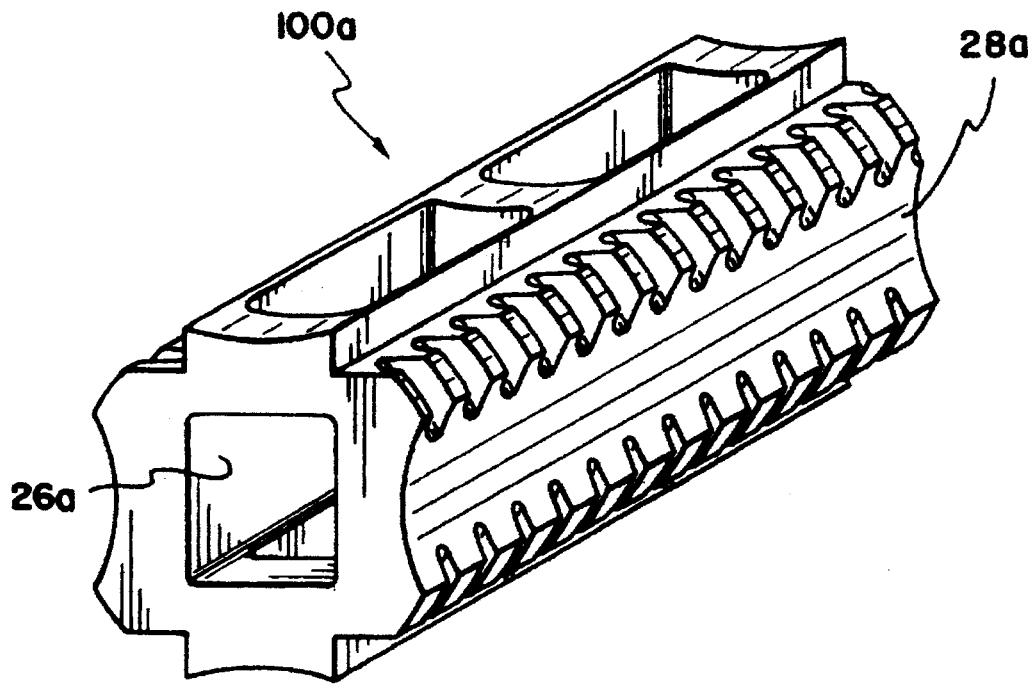
FIG. 15 is a perspective view of an implant alternative embodiment.

In the event a surgeon prefers not to use bone dowels 200 in the manner indicated in FIG. 12, it is desirable not to have the side wall openings 46 opposing disc material in order to prevent such disc material from entering into the implant 100 and interfering with bone growth through the implant 100. Accordingly, FIG. 15 shows an alternative embodiment implant 100a where the side walls 28a,26a are solid and do not include openings 46. Accordingly, there is no direct communication between the disc material and the interior of the implant 100a.

Figure 16:
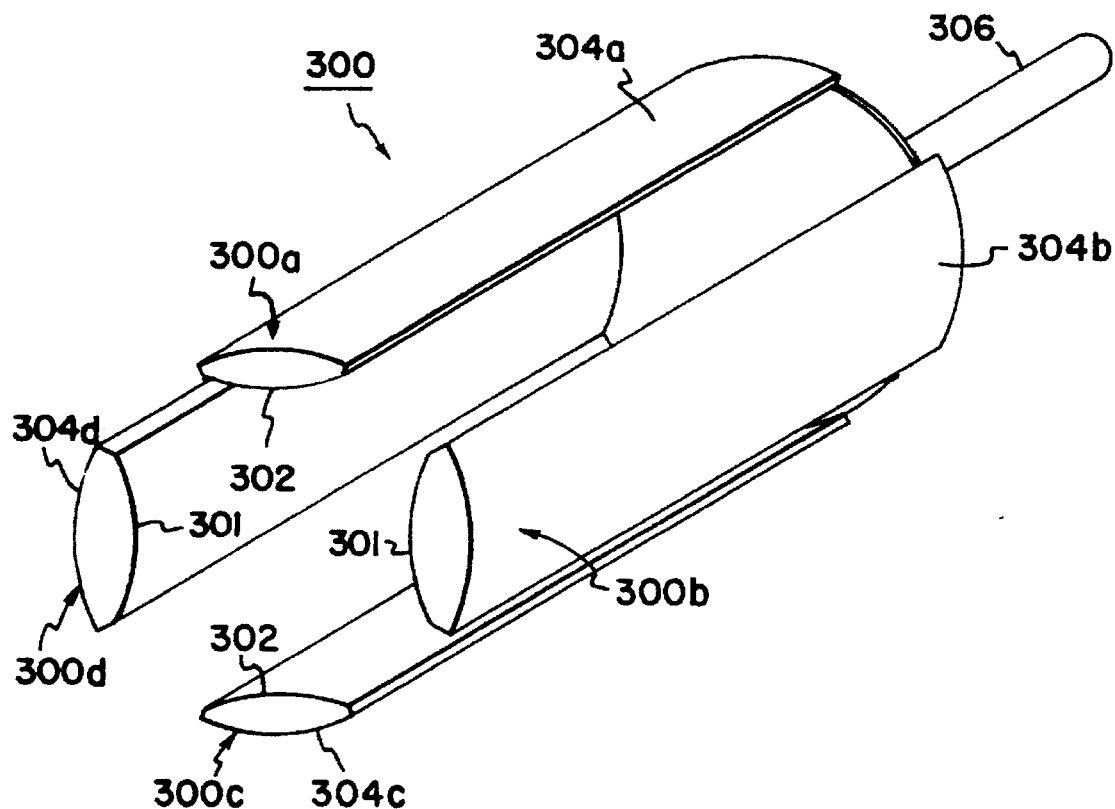
FIG. 16 is a view of a tool for placement of the implant within a bore.

FIG. 16 shows an insertion tool 300 for inserting the implant 100. The insertion tool 300 includes four prongs 300a–300d. The prongs 300a–300d cover the openings 44,46 with the thicker prongs 300d, 300b having convex inner surfaces 301 sized to complementary mate with the concave side walls 26,28. Further, the thinner prongs 300a, 300c have convex surfaces 302 sized to mate with the concave surfaces 30a,32a of the ridges 30,32. The insertion device 300 covers the holes 44,46 during insertion of the implant 100 to prevent disc material and other debris from entering the interior 40 of the implant 100. Also, the outer surfaces 304a–304d of each of the prongs is generally the arc of a cylinder such that the device 100 within the insertion tool 300 presents a cylindrical surface permitting the non-cylindrical implant 100 to be implanted into a round bore 102. A handle 306 connects the prongs and permits turning or axial driving of the tool 300.

As indicated, it is desirable that bores 44 be of maximum surface area as possible to increase the surface porosity of the implant 100. Applicants, through animal studies and human clinical experience, have found that the larger the surface porosity the greater the probability for successful bone ingrowth into the implant 100.

The present invention utilizes the anchors 50 embedded within the end plates 10a,12a to hold the implant 100 in position. Since the end plates 10a,12a are formed of cortical bone 10a,12a, the embedded anchors 50 within the end plates 10a,12a provide substantial force against inadvertent movement of the implant 100. Also, the anchors 50 permit either threading the implant 100 by rotating it about its axis X—X or by implanting while driving the implant 100 and tool 300 with a hammer or the like along its axis X—X. The square cross section anchor 50 is tapered (at $A_1$) to provide resistance to expulsion.

Having thus described the present invention in a preferred embodiment, it will be appreciated that the equivalents of the disclosed concepts such as those which readily occurred to one skilled in the art are intended to included within the scope of the claims which are appended hereto.

What is claimed is:

1. An implant for facilitating intervertebral fusion between opposing vertebrae, said implant comprising:

a hollow implant body having a generally parallelepiped configuration with longitudinal edges;

a plurality of generally linear and separate anchor segments disposed at said longitudinal edges and said anchor segments spaced from one another by unthreaded areas on surfaces of said body between said longitudinal edges;

said anchor segments cooperating to define a helical pattern;

said body having at least two diametrically opposed sides with openings formed through each of said sides in communication with an interior of said implant body.

2. An implant for facilitating intervertebral fusion between opposing vertebrae; said implant comprising:

an implant body having a first bearing surface and a second bearing surface, each of said first and second bearing surfaces extending generally parallel to one another and on opposite sides of a longitudinal axis of said body;

a first ridge extending from said first bearing surface;

a second ridge extending from said second bearing surface;

a first opening formed through said first ridge in communication with said interior;

a second opening formed through said second ridge in communication with said interior; and a plurality of anchor segments disposed on opposite sides of said first and second ridges with said plurality of anchor segments defining a helix pattern.

3. The implant according to claim 2 wherein said first and second bearing surfaces and first and second ridges are sized for said first and second bearing surface to oppose cortical bone of end plates of opposing vertebrae and with said ridges sized to extend beyond said cortical bone and be in communication with cancellous bone of said vertebrae.

4. The implant according to claim 2 comprising first and second side walls extending between said first and second bearing surfaces.

5. The implant according to claim 4 comprising first and second bores formed through said first and second side walls with first and second bores in communication with said interior.

6. The implant according to claim 4 wherein said side walls are concave along their longitudinal axis.

7. The implant according to claim 6 comprising first and second bores formed through said side walls with said first and second bores in communication with said interior.

8. The implant according to claim 7 wherein said implant is selected for placement within a bore formed between opposing vertebra with said bore having a predetermined radius, said anchor segments separated by valleys with a radial line from said longitudinal axis to said valleys being substantially equal to a said radius of said bore.

9. The implant according to claim 4 wherein said side walls are substantially solid throughout their surface area.

10. The implant according to claim 2 wherein said body is providing with a leading edge having a taper with a cross-sectional area of said body at said leading edge being smaller than a cross sectional area of said body away from said leading edge.

11. The implant according to claim 2 wherein said side walls and said bearing walls are concave along said longitudinal dimension.

12. The implant according to any of claims 2 or 1 wherein said anchor segments are thread segments.

13. An implant for facilitating intervertebral fusion between opposing vertebrae; said implant comprising:

an implant body having a first bearing surface and a second bearing surface, each of said first and second bearing surfaces extending generally parallel to one another and on opposite sides of a longitudinal axis of said body;

a first ridge extending from said first bearing surface;

a second ridge extending from said second bearing surface;

a first opening formed through said first ridge in communication with said interior;

a second opening formed through said second ridge in communication with said interior;

first and second side walls extending between said first and second bearing surfaces;

said side walls are concave along their longitudinal axis; and said side walls are substantially solid through their surface area.

* * * * *

UNITED STATES PATENT AND TRADEMARK OFFICE
CERTIFICATE OF CORRECTION

PATENT NO. : 5,658,337

DATED : AUGUST 19, 1997

INVENTOR(S) : KOHRS ET AL.

It is certified that error appears in the above-identified patent and that said Letters Patent is hereby corrected as shown below:

Col. 3, line 66: "$10a'$" should read --$10a"$--

Col. 4, line 2: "$10b'$" should read --$10b"$--

Col. 7, line 12: "acurate" should read --arcuate--

Signed and Sealed this

Sixteenth Day of March, 1999

*Attest:*

Q. TODD DICKINSON

*Attesting Officer*　　*Acting Commissioner of Patents and Trademarks*